United States Patent [19]

Grigoleit et al.

[11] Patent Number: 4,523,016

[45] Date of Patent: Jun. 11, 1985

[54] PROCESS FOR THE CATALYTIC DEHYDROGENATION OF PIPERIDINE

[75] Inventors: Georg Grigoleit, Dorsten; Rudolf Oberkobusch, Duisburg; Jüergen Stadelhofer, Dortmund; Kurt Matern, Duisburg, all of Fed. Rep. of Germany

[73] Assignee: Rütgerswerke Aktiengesellschaft, Frankfurt, Fed. Rep. of Germany

[21] Appl. No.: 513,197

[22] Filed: Jul. 13, 1983

[30] Foreign Application Priority Data

Jul. 20, 1982 [DE] Fed. Rep. of Germany ....... 3227022

[51] Int. Cl.$^3$ ............................................. C07D 213/02
[52] U.S. Cl. ....................................... 546/252; 546/250
[58] Field of Search ................................ 546/250, 252

[56] References Cited

FOREIGN PATENT DOCUMENTS

| 579146 | 6/1933 | Fed. Rep. of Germany | 546/252 |
| 1192648 | 1/1966 | Fed. Rep. of Germany | 546/252 |
| 745400 | 2/1956 | United Kingdom | 546/252 |

*Primary Examiner*—Alan L. Rotman
*Attorney, Agent, or Firm*—Beveridge, DeGrandi & Weilacher

[57] ABSTRACT

The catalytic dehydrogenation of piperidine to pyridine in the gas phase using hydrogen as the carrier gas is carried out with a silicon dioxide carrier activated with copper, nickel and chromium as the catalyst, the metals copper, nickel and chromium being present in an amount of 5–12:1–5:0.1–<0.7 parts by weight per 100 parts by weight of catalyst. The optimum hydrogen/piperidine molar ratio is 5:1, and purified and dried conversion gas from the dehydrogenation reaction is preferably recycled and used as the hydrogen.

6 Claims, No Drawings

PROCESS FOR THE CATALYTIC DEHYDROGENATION OF PIPERIDINE

The present invention relates to an improved process for the preparation of pyridine by the catalytic dehydrogenation of piperidine in the gas phase.

Pyridine and pyridine bases are important intermediate compounds used in organic chemistry, and especially in agrochemistry and pharmaceutical chemistry. Apart from the production of pyridine from a coal tar base, the synthetic processes chiefly practised hitherto have the disadvantages of being partly based on expensive petrochemical raw materials and, on the other hand, of giving, in addition to pyridine, a number of alkylated pyridines, as by-products, which are not always desirable.

Tetrahydrofurfuryl alcohol, which can be prepared by hydrogenation of furfuraldehyde is available as a raw material for the preparation of pyridine and is independent of raw materials of petroleum origin.

Furfuraldehyde is obtained from agricultural waste products containing pentosanes, the chief precursors of furfuraldehyde. Piperidine can be prepared by reacing ammonia with tetrahydrofurfuryl alcohol, and serves as the starting material for the process described here. These are methods and procedures known in the art.

Several processes are known for the preparation of pyridine from piperidine. They essentially differ in the catalysts used and the reaction temperatures, which are between 200° and 600° C., and in the amount of hydrogen which is used as the carrier gas in the process and is stated in the hydrogen:piperidine molar ratio. These molar ratios disclosed range from 4.8:1 to about 18:1.

Thus, German Pat. No. 1,192,648 and British Pat. No. 745,400 disclose gas phase dehydrogenation using Pt or Pd as the catalyst. Although the data relating to conversion and selectivity are attractive, it has been found that the noble metal catalysts are nevertheless sensitive to catalyst poisons such as sulfur, halogens or ammonia, so that their activity decreases after a short time. Especially after reactivating this catalyst, a very rapid loss in activity occurs.

German Pat. No. 579,146 discloses catalysis of the dehydrogenation of heterocyclic compounds by metals of Group VI of the Periodic Table, which may also be mixed with other metals, such as zinc, copper, cobalt, nickel, calcium or magnesium. In the example disclosed for the dehydrogenation of piperidine, tungsten oxide is used as the catalyst. However, a conversion of only 84% is achieved at 410° C., and a high percentage (10%) of undesirable condensation products is also obtained.

Similar, likewise unsatisfactory results in respect of reactivity and selectivity in the preparation of pyridine from piperidine are obtained by the chromium/copper catalyst system described in Z. obsc. Chim. 29 (1959) 440–443, English edition. Although a piperidine conversion of 86% is achieved at a reaction temperature of 400° C., the pyridine selectivity is only 53.2%.

There was thus the object of discovering a process for the catalytic dehydrogenation of piperidine to pyridine in which, in addition to a high conversion and a high selectivity for pyridine, long catalyst life times are achieved, so that an economical production of pyridine is made possible by this route.

This object is obtainable by the process according to this invention.

It has been found that a pyridine selectivity of 97% coupled with a high conversion can be achieved in the dehydrogenation of piperidine if a silicon dioxide activated with copper, nickel and chromium in an amount of 5–21:1–5:0.1–<0.7% by weight is used as the catalyst. Particularly good conversions are obtained with a metal ratio of 9:3:0.6.

In contrast to the teachings of German Pat. No. 579,146, it has been found that the metal of Group VI of the Periodic Table may be present only in traces of up to less than 0.7 percent by weight in the case of a catalyst with a high conversion and high selectivity for pyridine. In addition, the support is of importance. Thus, it has been found that better yields are achieved with silicon dioxide instead of aluminum oxide as the support.

As expected, fresh catalysts display the highest activity and begin to have a dehydrogenating action at temperatures from 300° C. During the consumption of the catalyst, a carbon deposit forms on the catalyst as a result of decomposition reactions and reduces the reactivity of the catalyst. In order to compensate for this, the reaction temperature is increased in the course of a prolonged period of use of the catalyst. In the process according to the invention, the dehydrogenation is carried out at temperatures between 300° and 420°, preferably between 345° and 380° C. It has been found that although the reactivity of the catalyst is reduced by an increasing deposit of carbon, its selectivity for pyridine is improved. Optimum conditions are achieved with a carbon content of 1 to 2%. If the carbon contest rises to 5–6%, the reactivity drops so that the catalyst must be reactivated. This is carried out in a known manner by passing oxygen over at temperatures of 400° to 440° C. and subsequently treating with hydrogen at temperatures of 150° to 350°.

The dehydrogenation of piperidine can be carried out continuously for months using only one charge of catalyst if the carbon deposited is always reduced again down to 1 to 2% when a reduction in the activity of the catalyst occurs. These very long catalyst life times are an essential advantage of the catalyst system according to the invention.

The piperidine to be dehydrogenated is vaporized in a vaporization device upstream of the reactor and is then passed over the catalyst using hydrogen as the carrier gas.

A hydrogen/piperidine molar ratio of 5:1 has been determined as the optimum amount of hydrogen. With this ratio, for example, the piperidine conversion is almost 20% higher than with a molar ratio of 3:1. On the other hand, a further increase in the amount of hydrogen available to a molar ratio of, for example, 8:1 leads to no further increase in conversion, and the space/time yield is reduced by the high hydrogen content.

Either fresh hydrogen or the conversion gas which is obtained during the dehydrogenation and chiefly contains hydrogen can be used as the hydrogen. A prerequisite for the use of the conversion gas is its purification and thorough drying.

For this, the portion of gas mixture obtained during the hydrogenation which is to be recycled to the reactor is washed with dilute sulfuric acid, dried thoroughly and passed over a molecular sieve. Apart from the fact that it is economically more favorable to circulate the conversion gas from the dehydrogenation reaction instead of using fresh hydrogen throughout the entire process, it is extremely surprising that by the operations, according to the invention, of purification and recycling of the conversion gas to the reactor, the piperidine conversion can be increased by more than 5% in comparison with the use of fresh hydrogen, although the selectivity shifts somewhat in favor of α-picoline. Traces of other gases, such as, for example, methane or carbon monoxide, still present in the purified conversion gas probably exert an additional catalytic effect.

As described herein the weight percent values of the metals in the catalyst are based on the metal per se. The weight basis of catalyst content is the combination of the weight of the metal and the silica support.

According to the invention the shapes of the silica carrier is not critical. Well known forms of silica include beads, pellets, honeycomb, powder, rings and the like. The silica support used for purpose of the invention is porous.

Known processes may be used to prepare the catalysts of the invention. For example, the silica can be impregnated with a corresponding salt solution all in one blend, then dried and heated so that the salts are decomposed to the oxides. Thereafter the catalyst and support are subjected to reduction, as with hydrogen, to produce the metals in the support. Conventional procedures are available to carry this out.

The examples and comparison examples which follow illustrate the process procedures according to the invention. In these examples, the yields, conversions and selectivities given are defined as follows:

$$\text{Yield: } \frac{\text{Amount of pyridine formed}}{\text{Maximum amount of pyridine expected}} \times 100$$

$$\text{Conversion: } \frac{\text{Moles of compound reacted}}{\text{Moles of compound fed in}} \times 100$$

$$\text{Selectivity: } \frac{\text{Moles of product obtained}}{\text{Moles of compound reacted}} \times 100$$

All the experiments were carried out in a glass tube reactor consisting of a preheating zone and the actual reactor section. The reactor has a length of 800 mm and a diameter of 20 mm. The preheating section is 350 mm long and has a diameter of 25 mm. The piperidine is vaporized from a 250 ml quartz flask. The reactor and vaporizer are heated by hot air, and the preheater is heated electrically. The catalyst charge is 55 g (100 ml). The catalyst particles are between 3 and 6 mm in diameter. Unless otherwise indicated, the catalysts mentioned have a carbon content of 1–2% at the start of the particular experiment as a result of dehydrogenation reactions which have in each case already been carried out beforehand or of regenerations.

EXAMPLE 1

24.3 g of piperidine/hour are fed into the vaporization flask by means of a metering pump. At the same time, 32.0 liters of fresh hydrogen/hour are passed in and the mixture is vaporized (hydrogen/piperidine molar ratio 5:1). The gas mixture present is heated to 380° C. in the preheating zone of the reactor. From here, it passes to the catalyst chamber, which is heated to 350° C. After the mixture has passed through the reactor, the reaction product is condensed. The conversion gas is removed with the exces hydrogen.

Catalyst: silicon dioxide containing 9% of Cu, 3% of Ni and 0.6% of Cr.

The condensed product is pyridine with small amounts of α-picoline and traces of other pyridine bases. In addition, the condensate contains piperidine which has not yet reacted. The pyridine and the other pyridine bases can be obtained from the condensate by suitable known processes, for example by fractional distillation. The piperidine thereby obtained is recycled again to the reactor for dehydrogenation.

| Result: | Piperidine conversion: | 84.5% |
|---|---|---|
| | Yield of pyridine: | 79.9% |
| | Selectivity for pyridine: | 93.1% |
| | Selectivity for α-picoline: | 0.6% |

After the experiment has lasted 60 hours, the carbon content and the activity of the catalyst are not substantially changed. Even after several reactivations of the catalyst, its activity does not change.

EXAMPLE 2

The dehydrogenation is carried out analogously to Example 1, but conversion gas (over 90% of hydrogen) which has been formed in a preceding dehydrogenation is used as the carrier gas instead of fresh hydrogen. After purification with 5% strength sulfuric acid and drying with calcium chloride and aluminum oxide, this gas is passed through a column filled with a molecular sieve 10A and is then recycled to the vaporization flask, the piperidine/gas ratio being maintained. The excess gas is removed.

| Result: | Piperidine conversion: | 89.9% |
|---|---|---|
| | Yield of pyridine: | 81.1% |
| | Selectivity for pyridine: | 88.8% |
| | Selectivity for α-picoline: | 4.1% |

After the experiment has lasted 60 hours, the carbon content and activity of the catalyst have not substantially changed.

EXAMPLE 3

The dehydrogenation of piperidine is carried out analogously to Example 1, but a hydrogen/piperidine molar ratio of 3:1 is used.

| Result: | Piperidine conversion: | 76.8% |
|---|---|---|
| | Yield of pyridine: | 72.7% |
| | Selectivity for pyridine: | 94.7% |
| | Selectivity for α-picoline: | 0.9% |

EXAMPLE 4 (Comparison Example)

The dehydrogenation of piperidine is carried out analogously to Example 1, but with the following catalyst: Al$_2$O$_3$ containing 9% of Cu, 3% of Ni and 0.6% of Cr.

| Result: | Piperidine conversion: | 57.9% |
|---|---|---|
| | Selectivity for pyridine: | 78.4% |

EXAMPLE 5 (Comparison Example)

The dehydrogenation of piperidine is carried out analogously to Example 1, but with the following catalyst: silicon dioxide containing 9% of Cu, 3% of Ni and 0.7% of Cr

| Result: | Piperidine conversion: | 61.6% |
|---|---|---|
| | Selectivity for pyridine: | 88.5% |

EXAMPLE 6 (Comparison Example)

The dehydrogenation of piperidine is carried out analogously to Example 1, but with the following catalyst: silicon dioxide containing 22% of Cu, 2% of $Cr_2O_3$ and 8% of $BaCrO_4$.

| Result: | Piperidine conversion: | 11.3% |
|---|---|---|
| | Selectivity for pyridine: | 85.4% |

EXAMPLE 7 (Comparison Example)

The dehydrogenation of piperidine is carried out analogously to Example 1, but with the following catalyst: 0.3% of Pd on $Al_2O_3$ (the catalyst is used in the fresh state).

| Result: | Piperidine conversion: | 81.4% |
|---|---|---|
| | Yield of pyridine: | 74.7% |
| | Selectivity for pyridine: | 91.8% |
| | Selectivity for α-picoline: | 2.9% |

After the first reactivation of the catalyst, a very rapid reduction in catalyst activity is observed, so that the piperidine conversion drops to 43.4% after a reaction time of only 18 hours.

We claim:

1. A process for the catalytic dehydrogenation of piperidine to pyridine in the gas phase using hydrogen as the carrier gas, which comprises contacting piperidine in the presence of hydrogen in a reaction zone with a catalyst comprising silicon dioxide activated with copper, nickel and chromium as the catalyst, the activating metals copper, nickel and chromium being present in an amount of 5–12:1–5:0.2–0.7 parts by weight per 100 parts by weight of catalyst, the hydrogen/piperidine molar ratio is 5:1, and carrying out the dehydrogenation reaction in the temperature range from 345° to 380° C., and thereafter separating and recovering the pyridine.

2. The process as claimed in claim 1, wherein the activating metals copper, nickel and chromium are present in an amount of 9:3:0.6 parts by weight per 100 parts by weight of the catalyst.

3. The process of claim 1, wherein the piperidine is vaporized and is thereafter passed over the catalyst using hydrogen as the carrier gas.

4. The process of claim 1, wherein subsequently a gaseous product is recovered from the dehydrogenation and a portion thereof which comprised hydrogen is recycled to the reaction zone.

5. The process as claimed in claim 4, wherein said portion of gaseous product is first dried and purified prior to recycling to the reaction zone for use as the carrier gas.

6. The process as claimed in claim 1, wherein a carbon deposit is formed on the catalyst during the reaction and amounts to 1 to 2% by weight of the catalyst weight.

* * * * *